United States Patent [19]

Koshi

[11] Patent Number: 4,699,512
[45] Date of Patent: Oct. 13, 1987

[54] DEVICE FOR MEASURING FLUORESCENCE POLARIZATION

[75] Inventor: Hiroyuki Koshi, Katsuta, Japan

[73] Assignee: Hitachi, Ltd., Tokyo, Japan

[21] Appl. No.: 754,925

[22] Filed: Jul. 15, 1985

[30] Foreign Application Priority Data

Jul. 13, 1984 [JP] Japan .................................. 59-146549

[51] Int. Cl.$^4$ ............................................ G01N 21/64
[52] U.S. Cl. .................................. 356/318; 250/458.1; 356/366
[58] Field of Search ............... 356/317, 318, 366, 367, 356/417; 250/225, 458.1, 459.1, 461.1, 461.2

[56] References Cited

U.S. PATENT DOCUMENTS 3,880,524 4/1975 Dill et al. .................... 250/225 X
4,299,486 11/1981 Nogami et al. .................... 356/318
4,429,230 1/1984 Honkawa et al. ............... 250/461.2

Primary Examiner—Vincent P. McGraw
Attorney, Agent, or Firm—Antonelli, Terry & Wands

[57] ABSTRACT

This invention relates to a device for measuring fluorescence polarization, which permits to measure the degree of fluorescence polarization in a short time and also its variations in time.

In order to achieve this object, a device for measuring fluorescence polarization according to this invention is provided with a control means permitting to set arbitrarily the polarization angle of the polarizer and that of the analyzer, by means of which the polarization angle of the polarizer or the analyzer is successively varied to arbitrary values so as to obtain polarization angles and fluorescence intensities corresponding thereto so that the degree of fluorescence polarization is obtained by using a plurality of the polarization angles and the fluorescence intensities corresponding thereto.

4 Claims, 5 Drawing Figures

DEVICE FOR MEASURING FLUORESCENCE POLARIZATION

BACKGROUND OF THE INVENTION

This invention relates to a device for measuring fluorescence polarization, and more particularly to a device for measuring fluorescence polarization permitting to measure the degree of fluorescence polarization in a short time and moreover suitable to measure its variations in time.

In a prior art device for measuring fluorescense polarization, as described in U.S. Pat. No. 4,299,486, an analyzer is rotated alternately to 0 (radian) and to $\pi/2$ (radian), and the parallel and orthogonal components of the polarization are measured with a predetermined interval. That is, according to such a prior art technique, in order to obtain a degree of fluorescence polarization, it is necessary to rotate the analyzer from 0 to $\pi/2$ and no measurement can be effected during the period of time when the analyzer is rotated from 0 to $\pi/2$. Consequently, the time during which measurements are effected is short with respect to the whole measurement time and thus efficiency is low.

Heretofore measurements of the degree of fluorescence polarization were effected, principally for the purpose of research, in order to know its variations before and after chemical reactions. Consequently, since chemical reactions were terminated and thus there were no variations of the degree of fluorescence polarization in time, measurement time did not need to be limited. Therefore, heretofore, in fluorescence polarization measurements it was possible to obtain satisfactory results by the method by which the analyzer was rotated between 0 and $\pi/2$ and the parallel and orthogonal components were separately measured.

Incidentally, recently, it is required in particular in the field of the immunology to measure variations of the degree of fluorescence polarization in time during the process of chemical reactions. However, in the case where variations of the degree of fluorescence polarization in time were measured, it was a problematical point that the variations in time could not be measured with a high precision, because, according to the prior art method by which the parallel and orthogonal components were measured separately, the interval between two successive measurements of the degree of fluorescence polarization is limited by the time necessary for the rotation of the analyzer.

SUMMARY OF THE INVENTION

The object of the invention is to provide a device for measuring fluorescence polarization permitting to measure the degree of fluorescence polarization in a short time and moreover suitable to measure its variations in time.

In order to achieve this object, a device for measuring fluorescence polarization according to this invention is provided with a control means permitting to set arbitrarily the polarization angle of the polarizer and that of the analyzer, by means of which the polarization angle of the polarizer or the analyzer is successively varied to arbitrary values so as to obtain polarization angles and fluorescence intensities corresponding thereto so that the degree of fluorescence polarization is obtained by using a plurality of the polarization angles and the fluorescence intensities corresponding thereto.

As the result, the interval between two successive measurements of the degree of fluorescence polarization can be set independently of the time necessary for the rotation of the polarizer or the analyzer and thus the time necessary for the measurement of the degree of fluorescence polarization for a sample is shortened. Further, alteration of the sample during the measurement is reduced and variations of the degree of fluorescence polarization in time can be measured with a high precision.

DESCRIPTION OF THE PREFERRED EMBODIMENT

Figure 1:
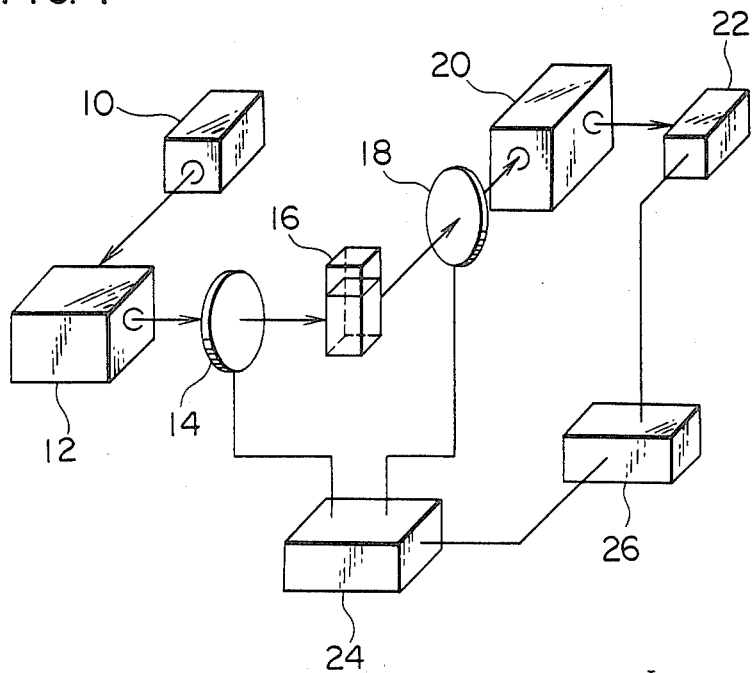
FIG. 1 is a scheme showing the construction of a device for measuring fluorescence polarization according to this invention.

In FIG. 1 the reference numeral 10 represents a light source for exciting the sample and emerging light from the light source 10 is polarized by a polarizer 14 and excites a sample 16, after having been separated into its spectral components by a spectroscope 12 on the excitation side. Fluorescence light produced by the excited sample 16 enters a spectroscope 20 on the fluorescence side through an analyzer 18 and after the light has been separated into its spectral components, its fluorescence intensity is measured by a detection system 22. On the other hand, the angular position of the polarizer 14 and that of the analyzer 18 are controlled by a control system 24. Measurement results obtained by means of a detection system 22 are processed in an arithmetic unit 26 so that the degree of fluorescence polarization is obtained.

Figure 2:
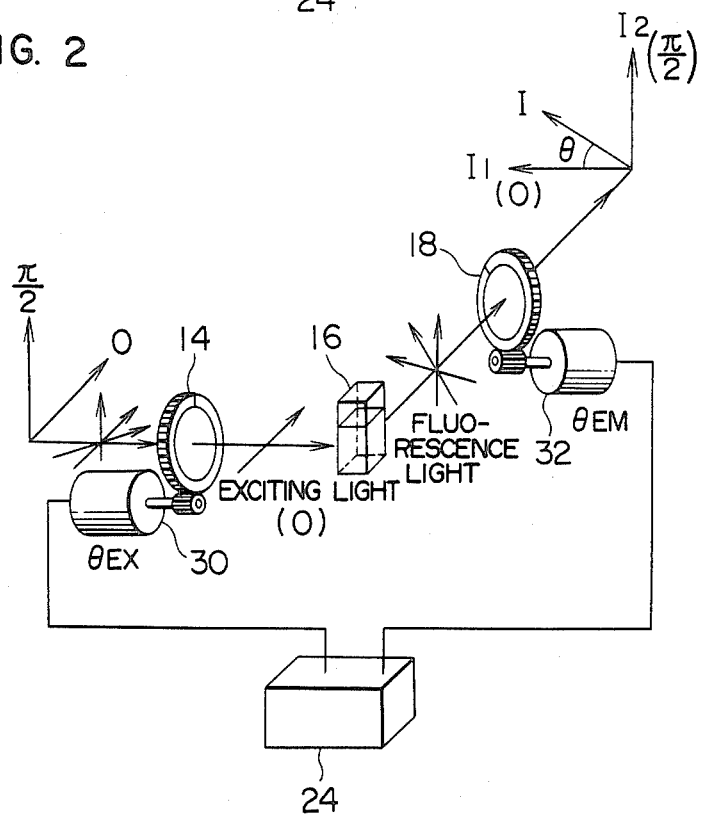
FIG. 2 is a scheme for explanation showing in detail principal parts in FIG. 1.
Figure 3:
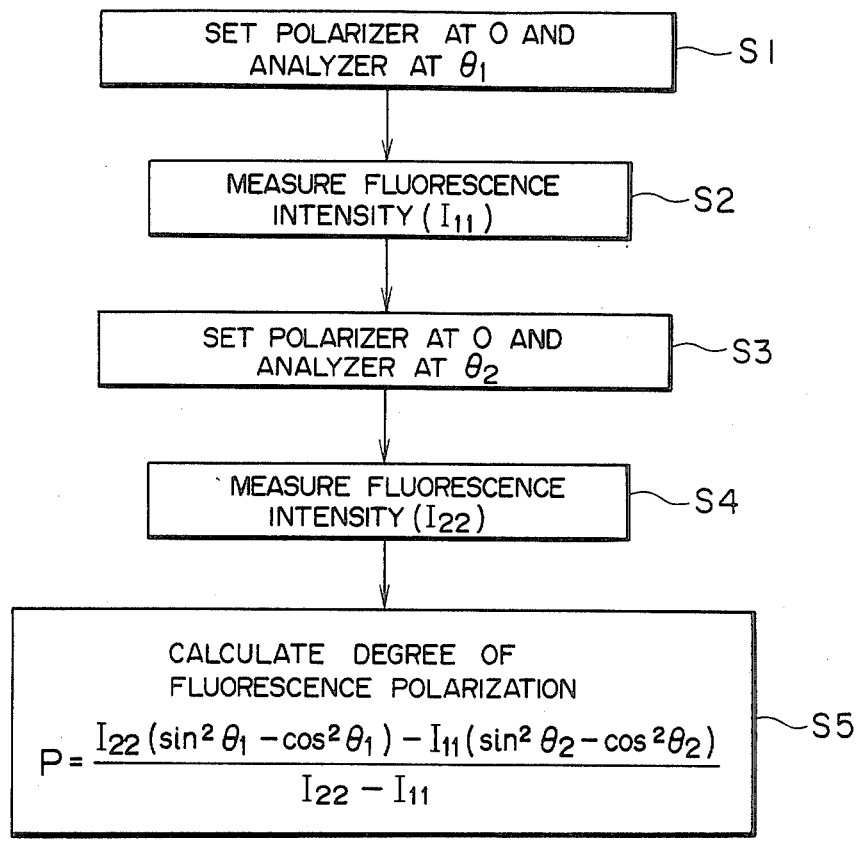
FIG. 3 is a flow chart for processing, when the degree of fluorescence polarization is measured.

As indicated in FIG. 2, the exciting light coming from the spectroscope 12 on the excitation side is polarized at a polarization angle $\theta_{EX}$ by the polarizer 14 and fluorescence light produced by the sample 16 with a polarization angle $\theta_{EM}$ is selected by the analyzer 18. The polarization angles $\theta_{EX}$ and $\theta_{EM}$ are obtained by controlling the rotation angle of the polarizer 14 and that of the analyzer 18 by means of pulse motors 30 and 32, respectively. These rotation angles are monitored by the control system 24 for subsequent operations.

Now, the fluorescence intensity I when the analyzer 18 is at an arbitrary angle $\theta$ can be represented by $$I = I_1 \cos^2\theta + I_2 \sin^2\theta \tag{1}$$

where $I_1$ and $I_2$ denote the parallel and the orthogonal component, respectively. Then, setting the polarization angle of the polarizer 14 $\theta_{EX}=0$ and the polarization angle of the analyzer 18 $\theta_{EM}=\theta_1$ (Step S1), the fluorescence intensity ($I_{11}$) is measured (Step S2). After that, setting $\theta_{EX}=0$ and $\theta_{EM}=\theta_2$ (Step S3), the fluorescence intensity ($I_{22}$) is measured (Step S4). Denoting the parallel component of the fluorescence intensity by $I_1$ and the orthogonal component by $I_2$, the following equations can be obtained by using Eq. (1):

$$I_{11} = I_1 \cos^2\theta_1 + I_2 \sin^2\theta_1 \qquad (2)$$

$$I_{22} = I_1 \cos^2\theta_2 + I_2 \sin^2\theta_2 \qquad (3)$$

Eqs. (2) and (3) are transformed as follows:

$$I_1 = \frac{I_{22} \sin^2\theta_1 - I_{11} \sin^2\theta_2}{\sin^2\theta_2 - \sin^2\theta_1} \qquad (4)$$

$$I_2 = \frac{I_{22} \cos^2\theta_1 - I_{11} \cos^2\theta_2}{\cos^2\theta_1 - \cos^2\theta_2} \qquad (5)$$

Consequently, the degree of fluorescence polarization can be represented by $$P = \frac{I_1 - I_2}{I_1 + I_2} \qquad (6)$$

$$= \frac{I_{22}(\sin^2\theta_1 - \cos^2\theta_1) - I_{11}(\sin^2\theta_2 - \cos^2\theta_2)}{I_{22} - I_{11}}$$

These operations are carried out by the arithmetic unit 26 and P is obtained (Step S5).

As explained above, it is not necessary to rotate the analyzer 18 by $\pi/2$ in order to obtain the degree of fluorescence polarization P, and the interval between two successive measurements of P can be determined independently of the time necessary for the rotation of the analyzer 18 so that the measurement time of the degree of fluorescence polarization P for a sample is shortened.

Furthermore, the angle $\theta$ and the fluorescence intensity I can be measured with a certain time interval while rotating the analyzer 18 either continuously or discontinuously. Moreover, $\theta_1$ and $\theta_2$ can be arbitrarily determined, and $I_1$ and $I_2$ can be mean values of results obtained for several sets of $\theta_1$ and $\theta_2$. Still further variations of the degree of polarization can be measured by varying the angle while rotating the polarizer 14 and fixing the analyzer 18.

Figure 4:
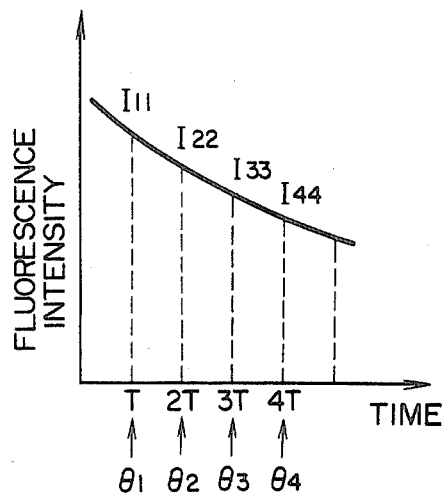
FIG. 4 is a diagram indicating the relation between the time interval for measurements and the fluorescence intensity at each point of time, when variations of the degree of fluorescence polarization in time are measured.
Figure 5:
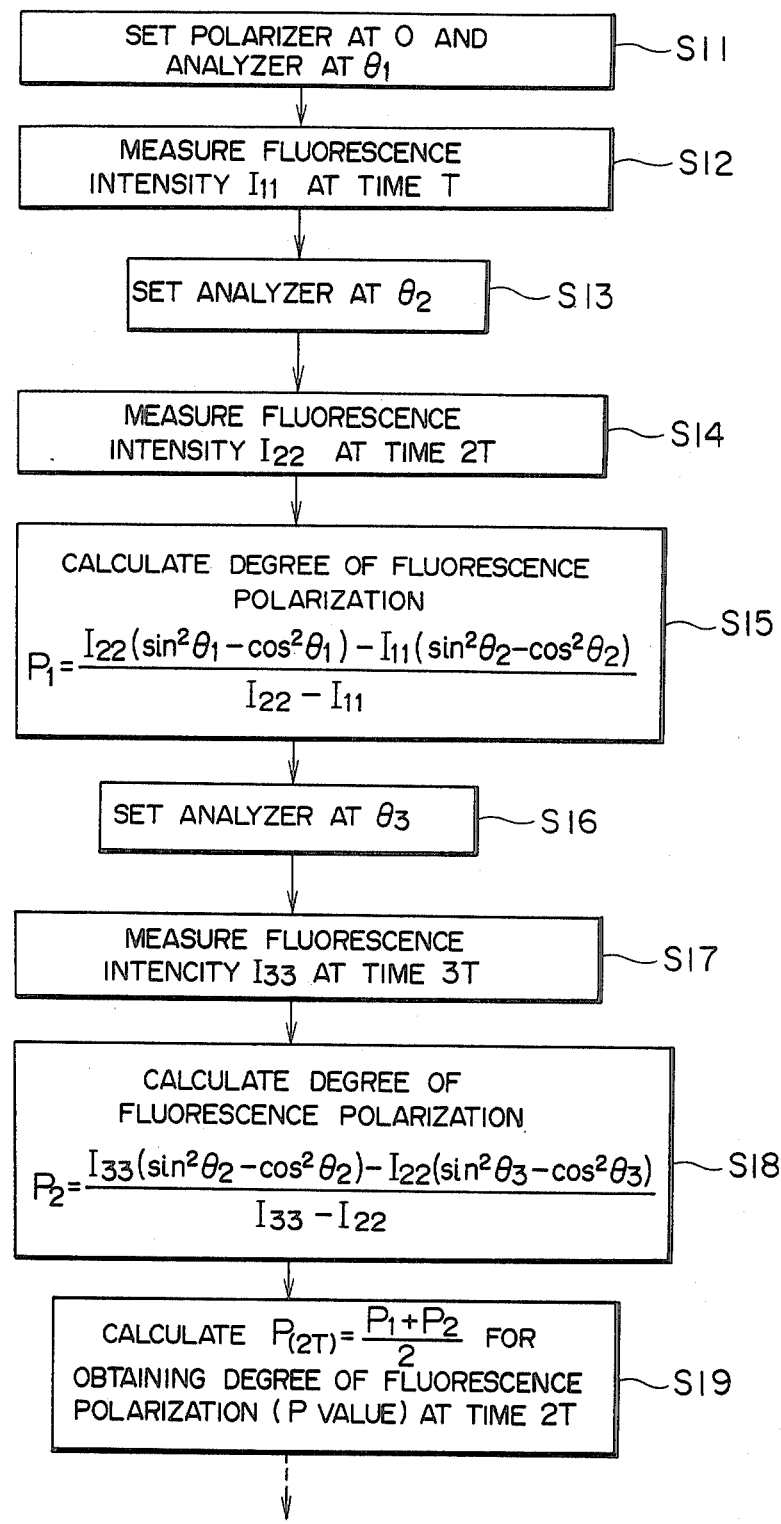
FIG. 5 is a flow chart for processing, when variations of the degree of fluorescence polarization in time are measured.

Next the method for measuring variations of the degree of fluorescence polarization in time will be explained. FIG. 4 is a diagram indicating the relation between the time interval for measurements and the fluorescence intensity at each point of time, and FIG. 5 is a flow chart for processing therefor. At first, setting the polarizer 14 at 0 and the analyzer 18 at $\theta_1$ (Step S11), the fluorescence intensity $I_{11}$ at a point of time T is measured (Step S12). Then, rotating only the analyzer 18 to $\theta_2$ (Step S13), the fluorescence intensity $I_{22}$ at a point of time 2T is measured (Step S14) and the degree of fluorescence polarization $P_1$ is calculated by using $\theta_1$, $\theta_2$, $I_{11}$ and $I_{22}$ at Step S15. Next, rotating only the analyzer 18 to $\theta_3$ (Step S16), the fluorescence intensity $I_{33}$ at a point of time 3T is measured (Step S17) and the degree of fluorescence polarization $P_2$ is calculated by using $\theta_2$, $\theta_3$, $I_{22}$ and $I_{33}$ at Step S18. At Step S19 $(P_1+P_2)/2$ is calculated and the value $P_{(2T)}$ thus obtained is adopted as the degree of fluorescence polarization at the point of time 2T. The similar procedure is repeated for following values.

In the case where the degree of fluorescence polarization varies in time, the parallel component $I_1$ and the orthogonal component $I_2$ cannot be regarded as constant. However, since they can be regarded as constant in a short time, as indicated above, the degree of fluorescence polarization at a certain measurement point of time can be obtained by measuring the angular position of the analyzer 18 and the fluorescence intensity with a certain time interval T and by calculating a mean value of degrees of fluorescence polarization calculated by using measured values for two points of time just before and after the certain point of time. By repeating this procedure, it is possible to obtain variations of the degree of fluorescence polarization in time with a certain time interval. Further, since the measurement time interval T can be arbitrarily determined, it is possible to measure the variations of the degree of fluorescence polarization with a satisfactorily high precision by using a sufficiently small T. Moreover, in this case, the number of measurement points of time for obtaining the mean values can be arbitrarily choosen, and also not the measurement time interval but the variation of the angle $\theta$ of the analyzer 18 can be held constant.

I claim:

1. Device for measuring fluorescence polarization comprising:
   a light source for exciting a sample;
   a spectroscope on the excitation side for separating light emerging from said light source into its spectral components;
   a polarizer for polarizing exciting light coming from said spectroscope on the excitation side;
   an analyzer for selecting a polarization of fluorescence produced by the sample excited by the exciting light coming from said polarizer;
   a spectroscope on the fluorescence side for separating fluorescence light coming from said analyzer into its spectral components;
   a detection system for measuring the intensity of fluorescence light coming from said spectroscope on the fluorescence side;
   a control system permitting to set arbitrarily the polarization angle of said polarizer and that of said analyzer; and
   an arithmetic unit for calculating the degree of fluorescence polarization on the basis of the output of said detection system;
   whereby the polarization angle of the polarizer or the analyzer is successively varied to arbitrary values between 0 and $\pi/2$ so as to obtain polarization angles and fluorescence intensities corresponding thereto so that the degree of fluorescence polarization is obtained by using a plurality of the polarization angles and the fluorescence intensities corresponding thereto.

2. Device for measuring fluorescence polarization according to claim 1, wherein the polarization angle of said polarizer and said analyzer is controlled by means of pulse motors.

3. Device for measuring fluorescence polarization comprising:
   a light source for exciting a sample;
   a spectroscope on the excitation side for separating light emerging from said light source into its spectral components;
   a polarizer for polarizing exciting light coming from said spectroscope on the excitation side;
   an analyzer for selecting a polarization of fluorescence produced by the sample excited by the exciting light coming from said polarizer;

a spectroscope on the fluorescence side for separating fluorescence light coming from said analyzer into its spectral components;

a detection system for measuring the intensity of fluorescence light coming from said spectroscope on the fluorescence side;

a control system permitting to set arbitrarily the polarization angle of said polarizer and that of said analyzer; and an arithmetic unit for calculating the degree of fluorescence polarization on the basis of the output of said detection system;

whereby the fluorescence intensity is measured at $\theta_1$ and $\theta_2$, when the polarization angle of said polarizer is fixed at 0 and that of the analyzer is varied from $\theta_1$ to $\theta_2$ between 0 and $\pi/2$ and the degree of fluorescence polarization is calculated on the basis of the values thus obtained.

4. Device for measuring fluorescence polarization comprising:

a light source for exciting a sample;

a spectroscope on the excitation side for separating light emerging from said light source into its spectral components;

a polarizer for polarizing exciting light coming from said spectroscope on the excitation side;

an analyzer for selecting a polarization of fluorescence produced by the sample excited by the exciting light coming from said polarizer;

a spectroscope on the fluorescence side for separating fluorescence light coming from said analyzer into its spectral components;

a detection system for measuring the intensity of fluorescence light coming from said spectroscope on the fluorescence side;

a control system permitting to set arbitrarily the polarization angle of said polarizer and that of said analyzer; and an arithmetic unit for calculating the degree of fluorescence polarization on the basis of the output of said detection system;

whereby the fluorescence intensity is measured at $\theta_1$, $\theta_2$ and $\theta_3$, when the polarization angle of said polarizer is fixed at 0 and that of the analyzer is set successively at $\theta_1$, $\theta_2$ and $\theta_3$ between 0 and $\pi/2$ and variations of the degree of fluorescence polarization in time are calculated on the basis of the values thus obtained.

* * * * *